United States Patent
Falter et al.

(10) Patent No.: US 9,639,056 B2
(45) Date of Patent: May 2, 2017

(54) ACOUSTICAL HOLOGRAPHY WITH MULTI-LEVEL SQUARE WAVE EXCITATION SIGNALS

(71) Applicant: General Electric Company, Schenectady, NY (US)

(72) Inventors: Stephan Falter, Huerth (DE); James Norman Barshinger, Lewistown, PA (US); Dirk Lange, Huerth (DE); Mark Howard Feydo, Lewistown, PA (US); Werner Lammerich, Huerth (DE)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 826 days.

(21) Appl. No.: 14/029,426

(22) Filed: Sep. 17, 2013

(65) Prior Publication Data
US 2015/0078125 A1    Mar. 19, 2015

(51) Int. Cl.
*G03H 3/00*    (2006.01)
*G01S 7/00*    (2006.01)
(Continued)

(52) U.S. Cl.
CPC .......... *G03H 3/00* (2013.01); *G01N 29/0663* (2013.01); *G01N 29/348* (2013.01); *G01S 7/523* (2013.01)

(58) Field of Classification Search
USPC ............................................................ 367/8
See application file for complete search history.

(56) References Cited

U.S. PATENT DOCUMENTS

| | | | | |
|---|---|---|---|---|
| 3,655,258 A | * | 4/1972 | Hildebrand | G03H 1/00 359/9 |
| 3,832,888 A | * | 9/1974 | Langlois | G01N 29/06 367/10 |

(Continued)

FOREIGN PATENT DOCUMENTS

| | | |
|---|---|---|
| DE | 2923687 A1 | 4/1981 |
| WO | 03/029808 | 4/2003 |

OTHER PUBLICATIONS

STMicroelectronics STHV748 High Speed Ultrasound Pulser Data Sheet—May 2012—28 pages.
(Continued)

*Primary Examiner* — James Hulka
(74) *Attorney, Agent, or Firm* — Barclay Damon, LLP

(57) ABSTRACT

Systems and methods are disclosed herein in which multi-level square wave excitation signals are used instead of or in addition to fully-analog excitation signals to drive an array of transceiver elements to create a sound field. Use of multi-level square wave excitation signals produces acceptable transceiver output with reduced complexity, cost, and/or power consumption as compared with use of fully-analog excitation signals. In addition, use of such signals facilitates system implementation using application-specific integrated circuits (ASICs) and is not as restricted in voltage level and speed. At the same time, the benefits and applications of fully-analog excitation signals (e.g., acoustic holography, beam superposition, signal-to-noise ratio (SNR) improvements, suppression of parasitic modes, increased material penetration, potential for coded pulsing algorithms and suppression of side lobes in ultrasonic field) can still be achieved with multi-level square wave excitation signals.

23 Claims, 12 Drawing Sheets

(51) Int. Cl.
*G01S 7/523* (2006.01)
*G01N 29/06* (2006.01)
*G01N 29/34* (2006.01)

(56) References Cited

U.S. PATENT DOCUMENTS

| | | | | |
|---|---|---|---|---|
| 3,911,729 A * | 10/1975 | Collins | ............... | G01H 9/002 359/901 |
| 3,964,052 A * | 6/1976 | Langlois | ............ | G01N 29/0663 367/10 |
| 3,983,529 A * | 9/1976 | Langlois | ............... | G01H 9/002 367/10 |
| 4,021,771 A * | 5/1977 | Collins | ............... | G01N 29/0609 342/180 |
| 4,165,647 A * | 8/1979 | Collins | ............... | G01S 15/897 73/603 |
| 4,222,273 A * | 9/1980 | Takahashi | ............ | G01N 29/0663 73/603 |
| 4,222,274 A * | 9/1980 | Johnson | ............... | A61B 8/0825 128/915 |
| 4,348,902 A | 9/1982 | Tachita et al. | | |
| 5,212,571 A * | 5/1993 | Garlick | ............... | G03H 3/00 359/9 |
| 5,833,614 A | 11/1998 | Dodd et al. | | |
| 6,023,660 A * | 2/2000 | Dory | ............... | G01S 7/52036 702/39 |
| 6,590,830 B1 * | 7/2003 | Garlick | ............... | G01N 29/075 359/901 |
| 6,757,215 B2 * | 6/2004 | Garlick | ............... | G01N 29/075 359/901 |
| 6,831,874 B2 * | 12/2004 | Garlick | ............... | G03H 3/00 359/901 |
| 6,900,914 B1 * | 5/2005 | Tanaka | ............... | G03H 1/0248 359/10 |
| 7,022,074 B2 * | 4/2006 | Kristoffersen | ........ | B06B 1/0215 310/317 |
| 7,181,356 B2 | 2/2007 | Coperet | | |
| 7,259,897 B2 * | 8/2007 | Garlick | ............... | G01N 29/0663 359/1 |
| 7,581,444 B2 * | 9/2009 | Maurer | ............... | G01N 29/07 73/597 |
| 7,824,335 B2 * | 11/2010 | Wodnicki | ............... | A61B 8/00 600/437 |
| 7,987,724 B2 * | 8/2011 | Takada | ............... | G01N 29/0645 600/447 |
| 8,226,561 B2 * | 7/2012 | McLaughlin | ............ | G01N 29/14 600/443 |
| 8,235,902 B2 * | 8/2012 | Chen | ............... | A61N 7/02 600/407 |
| 2002/0118600 A1 * | 8/2002 | Garlick | ............... | G03H 3/00 367/100 |
| 2003/0039000 A1 * | 2/2003 | Tanaka | ............... | G03H 1/0248 359/22 |
| 2003/0097066 A1 * | 5/2003 | Shelby | ............... | A61B 8/0833 600/443 |
| 2004/0037164 A1 * | 2/2004 | Garlick | ............... | G01N 29/075 367/8 |
| 2004/0254459 A1 | 12/2004 | Kristoffersen et al. | | |
| 2005/0203415 A1 * | 9/2005 | Garlick | ............... | A61B 8/0833 600/463 |
| 2006/0195273 A1 * | 8/2006 | Maurer | ............... | G01N 29/07 702/39 |
| 2008/0264171 A1 | 10/2008 | Wodnicki | | |
| 2009/0069677 A1 * | 3/2009 | Chen | ............... | A61N 7/02 600/439 |
| 2009/0241675 A1 * | 10/2009 | Takada | ............... | G01N 29/0645 73/641 |
| 2010/0268082 A1 * | 10/2010 | McLaughlin | ............ | G01N 29/14 600/443 |
| 2014/0211588 A1 * | 7/2014 | Falter | ............... | G01S 15/897 367/8 |

OTHER PUBLICATIONS

International Search Report and Written Opinion issued in connection with corresponding PCT Application No. PCT/US2014/049717 dated Nov. 6, 2014.

U.S. Appl. No. 13/750,582, entitled "Ultrasonic Holography Imaging System and Method" filed Jan. 25, 2013.

* cited by examiner

| C1 | C2 | C3 | C4 | C5 | OUTPUT |
|----|----|----|----|----|--------|
| 1  | 0  | 0  | 0  | 0  | +V1    |
| 0  | 1  | 0  | 0  | 0  | +V2    |
| 0  | 0  | 1  | 0  | 0  | -V1    |
| 0  | 0  | 0  | 1  | 0  | -V2    |
| 0  | 0  | 0  | 0  | 1  | GND    |

ACOUSTICAL HOLOGRAPHY WITH MULTI-LEVEL SQUARE WAVE EXCITATION SIGNALS

FIELD

The subject matter disclosed herein generally relates to ultrasonic holography imaging systems for use in generating three-dimensional images by acoustic waves, and more particularly, to methods for imaging features within physical items using ultrasonic holography.

BACKGROUND

In systems for use in non-destructive testing of physical items and in other fields, non-invasive techniques are often required in order to determine conditions within an interior of a physical item. Ultrasonic vibrations have the capability of penetrating into and reflecting out of, or passing through, a solid physical item. By analyzing alterations in the patterns and frequencies of the ultrasonic vibrations after they have passed through a physical item, a visual image of the physical item, including features within the physical item, can be generated.

Specifically, an ultrasonic generator causes an emitter or transmitter element (transducer) to produce a directed sound field that propagates into a physical item to be tested. Reflections of defects or features within the physical item are directed back to a receiver element. The transmitter and receiver elements can be separate components within an array, or can be the same individual component functioning both as an transmitter and a receiver (referred to as a "transceiver"); similar to the manner in which a speaker can also function as a microphone. The sound field generates electrical impulses within the receiver. The electrical impulses are converted into data, which is processed, e.g., to create a visual image, or to create signals for inclusion in automated production environments. Phased-array transducers are used to provide a series of separate sound impulses ("tone bursts") that can be separated in time from each other, to enable a directed sound field to be generated. For example, if an array of individual ultrasonic transducers is actuated so that tone bursts are emitted that are spaced apart in time a fixed amount between adjacent emitters, an angled planar sound wave can be generated.

BRIEF DESCRIPTION

Systems and methods are disclosed herein in which multi-level square wave excitation signals are used instead of or in addition to fully-analog excitation signals to drive an array of transceiver elements to create a sound field. Use of multi-level square wave excitation signals produces acceptable transceiver output with reduced complexity, cost, and/or power consumption as compared with use of fully-analog excitation signals. In addition, use of such signals facilitates system implementation using application-specific integrated circuits (ASICs) and is not as restricted in voltage level and speed. At the same time, the benefits and applications of fully-analog excitation signals (e.g., acoustic holography, beam superposition, signal-to-noise ratio (SNR) improvements, suppression of parasitic modes, increased material penetration, potential for coded pulsing algorithms, and suppression of side lobes in ultrasonic field) can still be achieved with multi-level square wave excitation signals.

In some embodiments, an ultrasonic holography system includes an ultrasonic transducer array including a plurality of transmitter elements configured to emit a plurality of ultrasonic waveforms toward a physical item, and a plurality of receiver elements configured to receive a plurality of return ultrasonic waveforms reflected from the physical item. The system also includes a processor system coupled to said ultrasonic transducer array. The processor system is configured to generate a plurality of outgoing multi-level square wave transmitter driving signals configured to cause said ultrasonic transducer array to emit said plurality of ultrasonic waveforms, wherein at least two of said plurality of ultrasonic waveforms are differentiated from each other through variation of at least one of amplitude, frequency, phase, time shift, and a modulation of any one thereof. The processor system is also configured to receive a plurality of incoming analog waveform signals, generated by said ultrasonic transducer array, said incoming analog waveform signals representative of at least a portion of said plurality of return ultrasonic waveforms. The processor system is also configured to process the plurality of incoming analog waveform signals to evaluate the internal structure of the physical item.

In some embodiments, a method for imaging a physical item using ultrasonic holographic imaging includes, using a processor system coupled to a memory device, defining an image structure using data stored in the memory device, the data representing a geometry of the physical item. The method also includes driving a plurality of ultrasonic transmitter elements of a transducer array coupled to the processor system with a plurality of multi-level square wave transmitter driving signals to cause the ultrasonic transducer array to emit a plurality of ultrasonic waveforms, wherein at least two of the of ultrasonic waveforms are differentiated from each other through variation of at least one of amplitude, frequency, phase, time shift, and a modulation of any one thereof.

In some embodiments, a system includes an ultrasonic transducer array including a plurality of transmitter elements configured to emit a plurality of ultrasonic waveforms, and a pulse generation circuit configured to generate a plurality of multi-level square wave transmitter driving signals configured to cause said ultrasonic transducer array to emit said plurality of ultrasonic waveforms, wherein at least two of said plurality of ultrasonic waveforms are differentiated from each other through variation of at least one of amplitude, frequency, phase, time shift, and a modulation of any one thereof.

Figure 1:
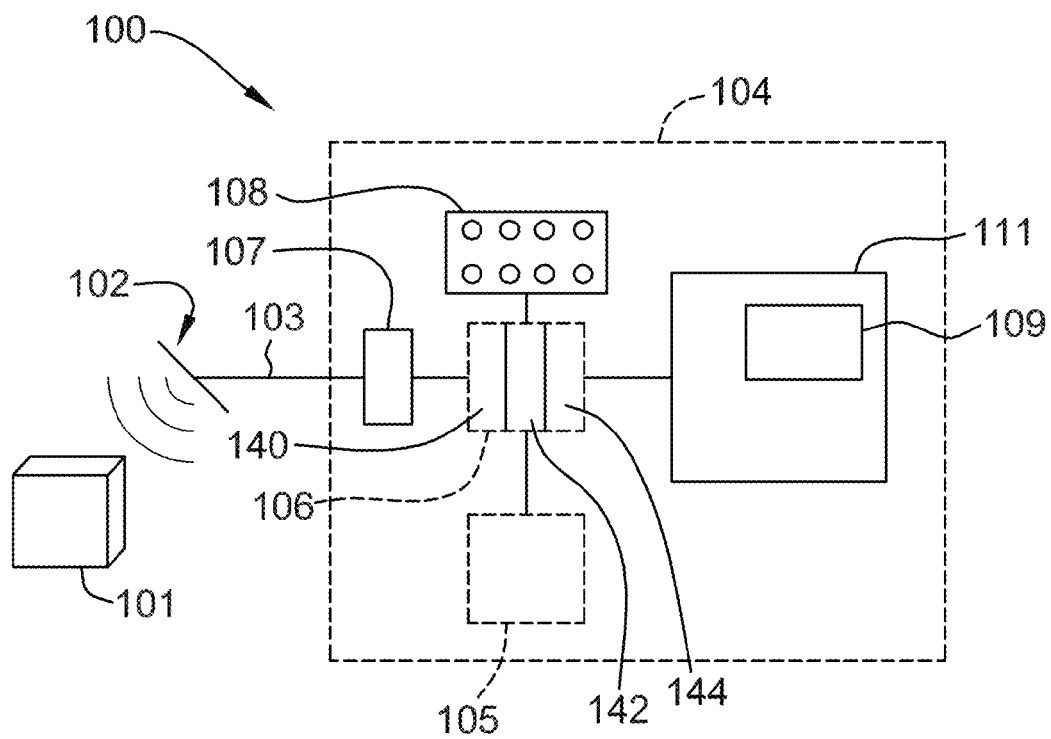
FIG. 1 is a schematic illustration of an exemplary ultrasonic holography system and an environment in which the system is used.

It is noted that the drawings are not necessarily to scale. The drawings are intended to depict only typical aspects of the subject matter disclosed herein, and therefore should not be considered as limiting the scope of the disclosure. In the drawings, like numbering represents like elements between the drawings.

DETAILED DESCRIPTION

Certain exemplary embodiments will now be described to provide an overall understanding of the principles of the structure, function, manufacture, and use of the devices, systems, and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Ultrasonic holography imaging systems that use analog excitation signals are capable of producing detailed sound fields that are not constrained by the configuration of the transducer array, so as to provide enhanced imaging that is capable of addressing the shape and configuration of the physical item being imaged. The analog excitation signals can have varying amplitude, frequency, phase, time shift, or modulation of any of said parameters across transducer elements to achieve these effects.

Production of such analog excitation signals, however, requires complex and expensive circuitry and consumes a large amount of power. In addition, systems that use such signals are not readily amenable to implementation using ASICs, are restricted in the voltage levels that can be used for the excitation pulse, and are limited in terms of speed.

Accordingly, systems and methods are disclosed herein in which multi-level square wave excitation signals are used instead of or in addition to fully-analog excitation signals to drive an array of transceiver elements to create a sound field. Use of multi-level square wave excitation signals produces acceptable transceiver output with reduced complexity, cost, and/or power consumption as compared with use of fully-analog excitation signals. In addition, use of such signals facilitates system implementation using application-specific integrated circuits (ASICs) and is not as restricted in voltage level and speed. At the same time, the benefits and applications of fully-analog excitation signals (e.g., acoustic holography, beam superposition, signal-to-noise ratio (SNR) improvements, suppression of parasitic modes, increased material penetration, potential for coded pulsing algorithms, and suppression of side lobes in ultrasonic field) can still be achieved with multi-level square wave excitation signals.

As used herein, the terms multi-level square wave and multi-level rectangular wave are used interchangeably to refer to signals having a plurality of square or rectangular pulses or steps at discrete amplitude levels (positive and/or negative).

FIG. 1 is a schematic illustration of an exemplary ultrasonic holography imaging system 100 for use in performing ultrasonic holographic imaging of a physical item 101. The system 100 includes an ultrasonic transducer array 102 coupled to a processing system 104 via a connection 103.

The ultrasonic transducer array 102 emits ultrasonic pulses and also receives ultrasonic waves that are reflected off of the physical item 101. More specifically, ultrasonic waves emitted by the transducer array 102 penetrate into the physical item 101 and reflect off of structures within the physical item 101, such as areas of decreased density (which may be suggestive of corrosion) or other flaws or variations within the physical item 101. The ultrasonic transducer array 102 is a rectangular array (m times n units) of ultrasonic transceiver elements 110 (illustrated in FIG. 2). While a rectangular array is shown in the illustrated embodiment, it will be appreciated that other array types can be used, including any multi-element transducer array with a fixed geometric positioning of the individual transceiver elements. Exemplary array types include, without limitation, those having angular segments of concentric rings and/or sparse arrays in which not all possible positions are populated with transceiver elements. Each ultrasonic transceiver element is a piezoelectric transceiver element. It will be appreciated, however, that other types of ultrasonic transceiver elements can be used instead or in addition, such as electromagnetic acoustic transducers ("EMATs") or capacitive micromachined ultrasonic transducers ("CMUTs"). Each ultrasonic transceiver element 110 is configured to transmit and receive ultrasonic waveforms. It will be appreciated that separate transmitter and receiver elements can be used instead of or in addition to the common transceiver elements.

The connection 103 can be any suitable connection device(s) sufficient to enable the system 100 to function as described herein, including, for example, a hard-wired arrangement.

The processing system 104 includes an analog processing section 107 coupled to a digital processing section 106. The digital processing section 106 is coupled to a memory or other storage device 105 and a user input device 108 (e.g., a control panel, keyboard, keypad, or other device or devices). The digital processing section 106 provides signals to a display 111 to generate a display image 109.

In operation, several series of "shots" of the physical item 101 are taken while imaging the physical item 101. Accordingly, the ultrasonic transducer array 102 is moved to a first position relative to the physical item 101, and one or more series of ultrasonic pulses are emitted towards the physical item 101. Reflections of those ultrasonic pulses are received by the ultrasonic transducer array 102 and data corresponding to the emitted pulses and corresponding received reflections is stored and processed. The ultrasonic transducer array 102 is then moved to another position relative to the physical item 101 and another series of "shots" is taken. The number of shots taken and positions used is dependent upon the configuration of the physical item 101 and the type of data that is being acquired (e.g., imaging to detect flaws, etc.).

The ultrasonic transducer array 102 can be caused by the digital processing section 106 to emit ultrasonic waveforms that, upon contact with the physical item 101, in turn cause a variety of different waveforms to propagate through the physical item 101. Exemplary waveforms include compression waves or shear waves which penetrate into the interior of the physical item and are used to check for cracks or the detection of internal flaws, Rayleigh waves, which are typically confined to the surface of the physical item and are used, for example, in analyzing or determining mechanical and structural properties of a material, such as cracking; Lamb waves, which typically travel along the wall of a physical item and are used, for example, to find and characterize internal flaws and cracks in the physical item; and creep waves, which typically serve to access areas hidden below other parts of the physical item, e.g., welds or solders.

Figure 2:
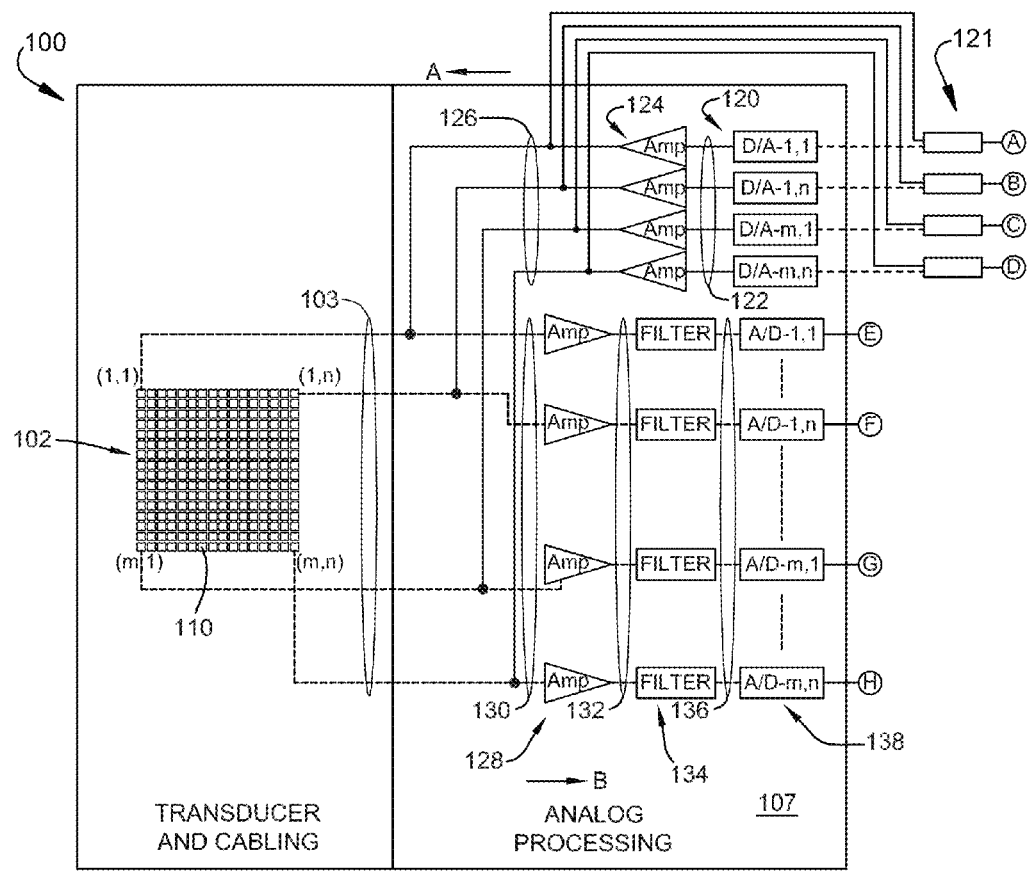
FIG. 2 is a portion of a circuit diagram illustrating the system of FIG. 1.
Figure 3:
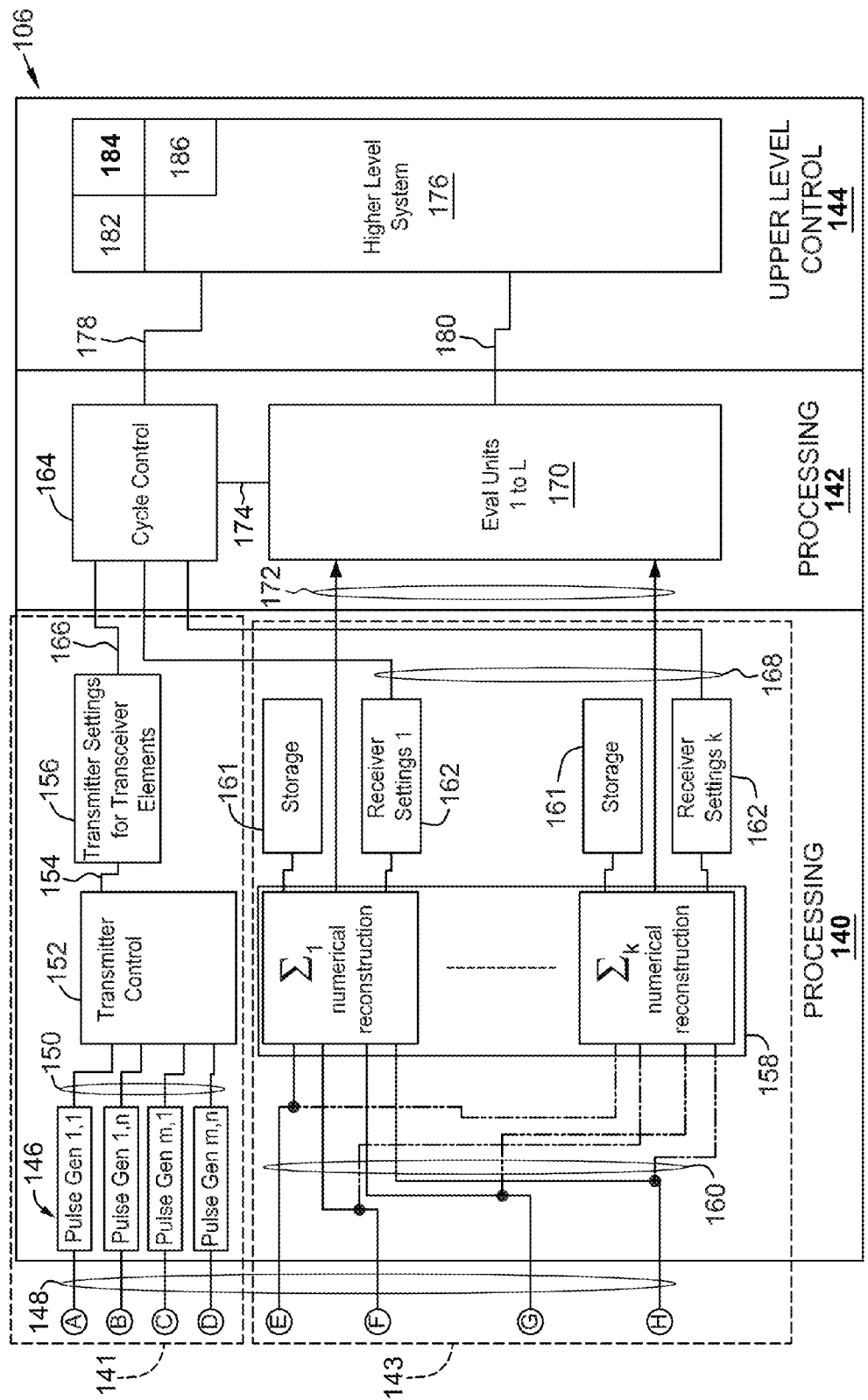
FIG. 3 is a further portion of a circuit diagram illustrating the system of FIG. 1.

FIGS. 2 and 3 together form a circuit diagram illustrating the system 100. Specifically, FIG. 2 depicts the ultrasonic transducer array 102 and the analog processing section 107 and FIG. 3 depicts the digital processing section 106.

Figure 17:
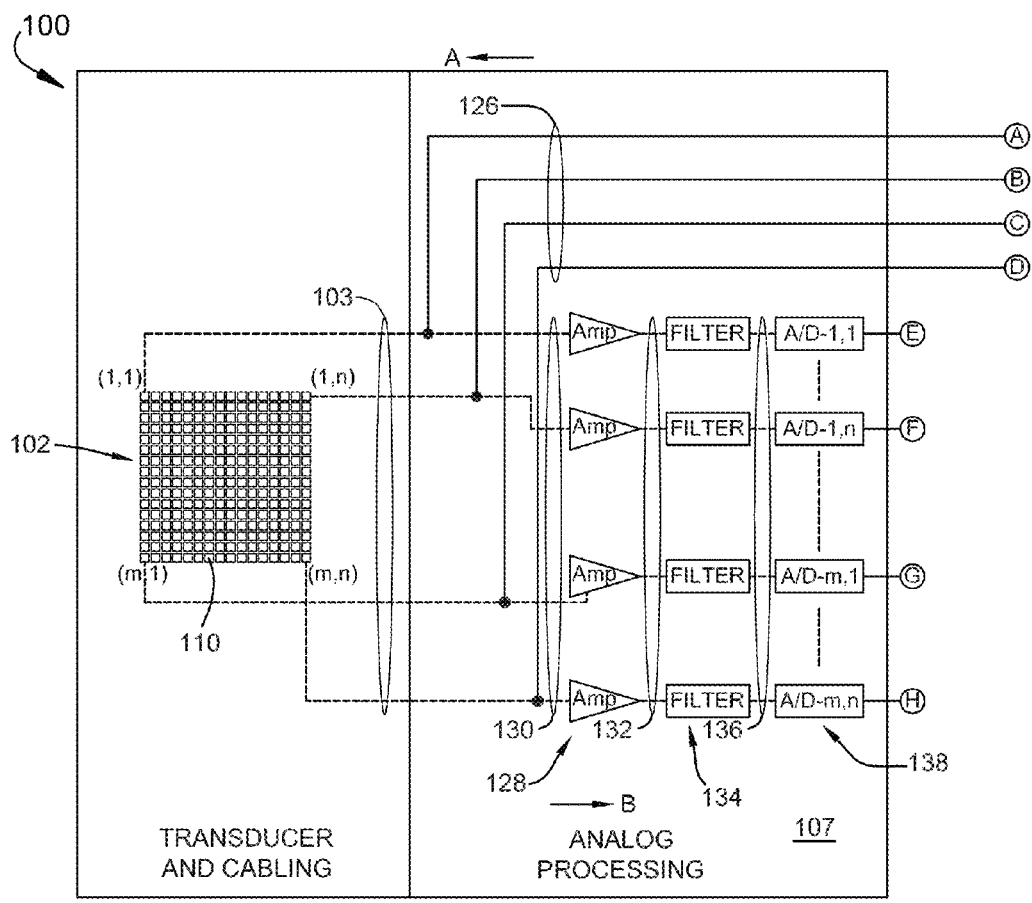
FIG. 17 is a portion of a circuit diagram illustrating another exemplary embodiment of an ultrasonic holography system.
Figure 18:
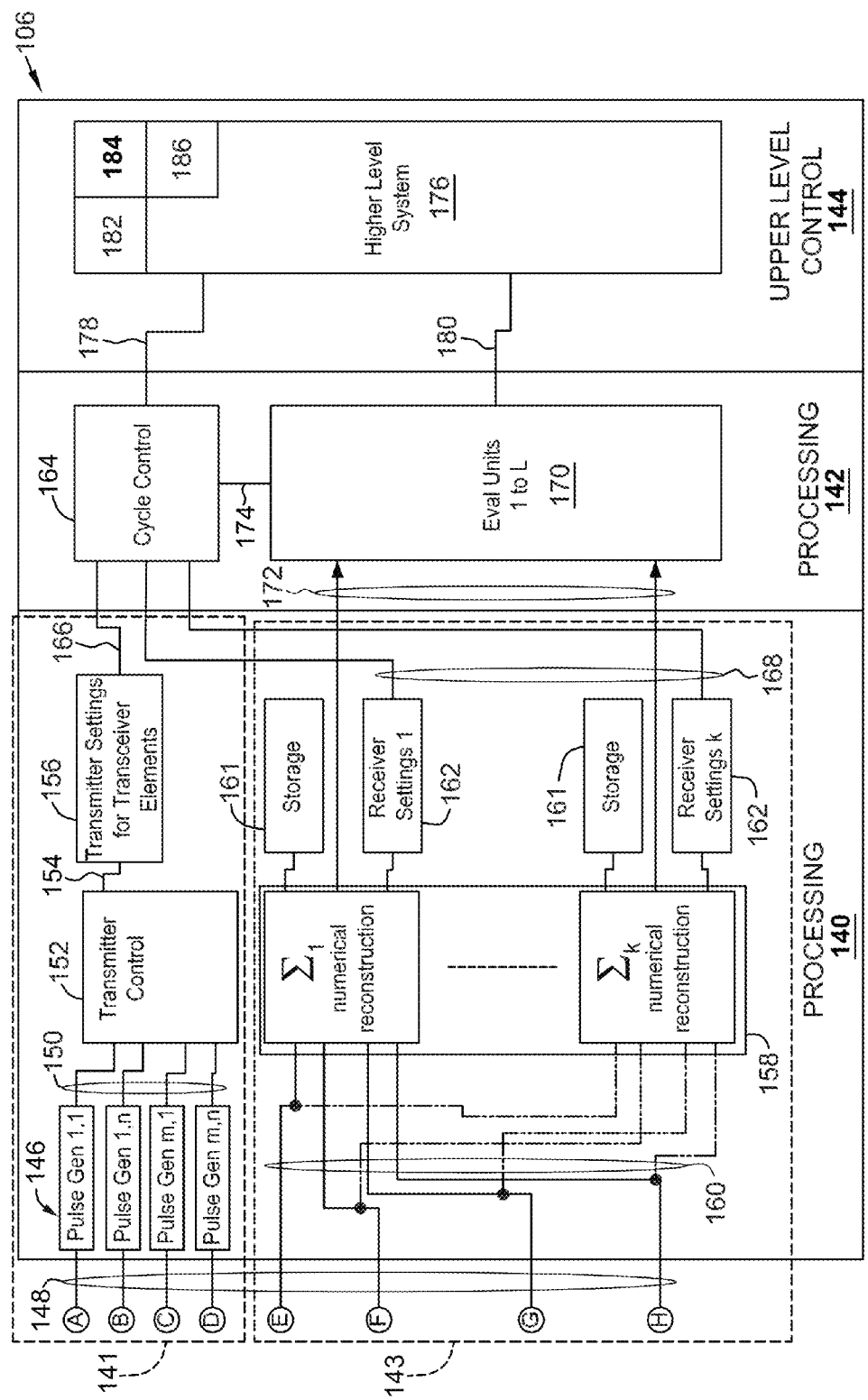
FIG. 18 is a further portion of the circuit diagram of FIG. 17.

The analog processing section 107 performs preprocessing of signals transmitted between the ultrasonic transducer array 102 and the digital processing section 106. The analog processing section 107 also allows for switching between operating modes of the system 100. As described in detail below, the system 100 is operable in a first mode in which multi-level square wave excitation pulses are used and a second mode in which fully-analog excitation pulses are used. It will be appreciated, however, that the system need not necessarily include provisions for operating in the second mode, in which case circuitry required for generating fully-analog excitation pulses can be omitted, as discussed below and as shown in FIGS. 17-18. It will further be appreciated that the system can operate in any of a number of hybrid modes of operation, in which one or more of the transceiver elements 110 are driven by multi-level square wave excitation pulses and one or more other transceiver elements are driven by fully-analog excitation pulses.

In the first mode of operation, the analog processing section 107 forwards excitation signals generated by the digital processing section 106 to the ultrasonic transducer array 102 (as indicated by an arrow A pointing to the left) to stimulate selected ones of the ultrasonic transceiver elements 110. In the second mode of operation, the analog processing section 107 converts digital signals generated by the digital processing section 106 into analog signals and amplifies the analog signals before forwarding them to the ultrasonic transducer array 102.

In either mode of operation, the analog processing section 107 also converts analog signals transmitted from the ultrasonic transceiver elements 110, that represent ultrasonic waves reflected from the physical item 101 and received by the ultrasonic transceiver elements 110, into digital signals and transmits those digital signals to the digital processing section 106 (as indicated by an arrow B pointing to the right).

The analog processing section 107 includes a plurality of switching devices 121 configured to selectively couple the outputs of a respective plurality of pulse generators 146 (shown in FIG. 3) to different locations in the analog processing circuitry depending on the selected operating mode of the system 100. In particular, in the first mode of operation, the switching devices 121 are configured such that the outputs of the pulse generators 146 are coupled directly to the ultrasonic transceiver elements 110 (via a plurality of connections 126 and a plurality of connections 103). In the second mode of operation, the switching devices 121 are configured such that the outputs of the pulse generators 146 are coupled to a plurality of digital-to-analog ("D/A") converters 120, which are in turn coupled via a plurality of connections 122 to a corresponding plurality of amplifiers 124. The amplifiers 124 are coupled, via the plurality of connections 126 and the plurality of connections 103 to corresponding ones of the ultrasonic transceiver elements 110.

Although only four sets of switching devices 121, D/A converters 120, amplifiers 124, and connections 103 are shown, it is understood that a set of these components is provided for, and coupled to, each of the ultrasonic transceiver elements 110.

The analog processing section 107 also includes a plurality of amplifiers 128 that are coupled, via connections 130, to the connections 103, and in turn to respective ones of the ultrasonic transceiver elements 110. Although only four amplifiers 128 are illustrated, it is understood that there is an amplifier 128 coupled to each of the ultrasonic transceiver elements 110. Each of the amplifiers 128 is coupled, via a plurality of connections 132 to a respective one of a plurality of filters 134. Each of the filters 134 is coupled, via a plurality of connections 136, to a corresponding one of a plurality of analog-to-digital ("A/D") converters 138. The filters 134 can be any suitable electronic signal filters necessary to enable the system 100 to function as described herein. The A/D converters 138 convert electronic waveforms received by the ultrasonic transceiver elements 110 and transmitted to the A/D converters 138 into digital signals.

The analog processing section 107 is coupled to the digital processing section 106. As shown in FIG. 3, the digital processing section 106 includes a primary digital processing section 140, a secondary digital processing section 142, and an upper level control section 144. The primary digital processing section 140 includes a waveform shaping section 141 and an image reconstruction and evaluation section 143.

In the waveform shaping section 141, a plurality of pulse generators 146 are coupled via a plurality of connections 148 to corresponding ones of the switching devices 121 (shown in FIG. 2). The pulse generators 146 are also coupled via a plurality of connections 150 to a transmitter control unit 152. The transmitter control unit 152 controls the pulse generators 146, depending on the operating mode of the system 100, to generate multi-level square wave excitation pulses, fully-analog excitation pulses, and/or a combination thereof. The transmitter control unit 152 optionally controls the pulse generators 146 to generate the excitation pulses by varying factors such as amplitude, frequency, phase, time shift, amplitude modulation, phase modulation, and frequency modulation with respect to each transceiver element 110. In embodiments in which the capability to generate fully-analog excitation pulses is omitted (e.g., the embodiment shown in FIGS. 17-18), the pulse generators 146 can be simpler pulse train generators specifically configured to generate multi-level square wave excitation pulses.

The transmitter control unit 152 is coupled via a connection 154 to a transmitter settings unit 156. The transmitter settings unit 156 stores and monitors settings for the ultrasonic transceiver elements 110 required to generate a specifically shaped ultrasonic pulse field, including selection of excitation pulse type as well as excitation pulse timing, magnitude, amplitude, frequency, time shift, and modulations of any thereof, for each pulse emitted by each ultrasonic transceiver element 110. The ultrasonic pulses propagate into the material area, where they interfere with each other. The result of this interference process is an acoustic image created inside the material.

In the image reconstruction and evaluation section 143, a summation unit 158 is coupled to each of the A/D converters 138 (shown in FIG. 2) via a plurality of connections 160. Each A/D converter 138 produces a single element digitized signal (also referred to as an "A-scan"). In order to perform a numerical reconstruction of the reflected sound field embodied in the individual A-scans, the summation unit 158 performs a summation process (also referred to as "numerical reconstruction") on the data signals received from each of the piezoelectric units, to produce a virtual A-scan of the complete physical item 101. In the illustrated embodiment, the summation unit 158 is configured as units in a plurality of FPGAs, though it will be appreciated that other components may be used in place of or in addition to FPGAs, such as ASICs.

In an exemplary summation process, the summation unit 158 sums the single element A-scans pointwise in time (using fixed time-steps (t0, t1, t2, . . . tFinal)). Accordingly, if the A-Scans are AScan_1(t0, t1, t2, . . . tn), AScan_2(t0, t1, t2, . . . tn), etc., to AScan_m(t0, t1, t2, . . . tn), then $$A\text{-}ScanSum(t0) = AScan\_1(t0 + \Delta t(1)) + AScan\_2(t0 + \Delta t(2)) + \ldots + AScan\_m(t0 + \Delta t(m))$$

$$A\text{-}ScanSum(t1) = AScan\_1(t1 + \Delta t(1)) + AScan\_2(t1 + \Delta t(2)) + \ldots + AScan\_m(t1 + \Delta t(m))$$

through $$A\text{-}ScanSum(tFinal) = AScan\_1(tFinal + \Delta t(1)) + AScan\_2(tFinal + \Delta t(2)) + \ldots + AScan\_m(tFinal + \Delta t(m))$$

With $tFinal \leq tn - \text{maximum}(\Delta t(1), \ldots, \Delta t(m))$ which results in a single summed A-Scan. The summation process is continued, during which various factors may be varied, including the contributing number of single element A-scans and the time delay between tone bursts of adjacent piezoelectric elements $\Delta t(x)$. Selection of factors to be varied is accomplished using ultrasonic testing and/or beamforming techniques known to those skilled in the art.

Another exemplary reconstruction method is a holographic reconstruction, where the summation of the m AScans is not only given with one point but according to an analog pulse train function comparable to the transmitter function. Accordingly, if the A-Scans are AScan_1(t0, t1, t2, . . . tn), AScan_2(t0, t1, t2, . . . tn), etc. to AScan_m(t0, t1, t2, . . . tn), and the holographic reconstruction pulse trains are H_1(t0, t1, . . . tj), H_2(t0, t1, . . . tk) to H_m(t0, t1, . . . tl), $$\begin{aligned}
A\text{-}ScanSum(t0) = &H\_1(t0) * AScan\_1(t0) + H\_1(t1) * AScan\_1(t1) + \ldots + \\
&H\_1(tj) * AScan\_1(tj) + \\
&H\_2(t0) * AScan\_2(t0) + \ldots + H\_2(t1) * \\
&AScan\_2(t1) + \ldots + \\
&+ H\_2(tk) * AScan\_2(tk) + \ldots + \\
&+ H\_m(t0) * AScan\_m(t0) + \ldots + H\_m(t1) * \\
&AScan\_m(t1) + \ldots + \\
&+ H\_m(t1) * AScan\_m(t1)
\end{aligned}$$

$$\begin{aligned}
A\text{-}ScanSum(t1) = &H\_1(t0) * AScan\_1(t1) + H\_1(t1) * AScan\_1(t2) + \ldots + \\
&H\_1(tj) * AScan\_1(tj) + \\
&H\_2(t0) * AScan\_2(t1) + \ldots + H\_2(t1) * \\
&AScan\_2(t2) + \ldots + \\
&H\_2(tk) * AScan\_2(t(k+1)) + \ldots + \\
&H\_m(t0) * AScan\_m(t1) + \ldots + H\_m(t1) * \\
&AScan\_m(t2) + \ldots + \\
&H\_m(t1) * AScan\_m(t(L+1))
\end{aligned}$$

through $$\begin{aligned}
A\text{-}ScanSum(tFinal) = &H\_1(t0) * AScan\_1(tFinal) + \\
&H\_1(t1) * AScan\_1(t(Final+1)) + \ldots + \\
&H\_1(tj) * AScan\_1(t(Final+j)) \\
&H\_2(t0) * AScan\_2(tFinal) + \\
&H\_2(t1) * AScan\_2(t(Final+1)) + \ldots + \\
&H\_2(tk) * AScan\_2(t(Final+k)) + \ldots + \\
&H\_m(t0) * AScan\_m(tFinal) + \\
&+ H\_m(t1) * AScan\_m(t(Final+1)) + \ldots + \\
&+ H\_m(tL) * AScan\_m(t(Final+L))
\end{aligned}$$

As long as Final+j or Final+k or Final+L are smaller than the number of samples n.

In yet another exemplary embodiment, a reconstruction based on a combination of a fixed correction and a holographic correction can be used.

The image reconstruction and evaluation section 143 further includes a plurality of storage elements 161 for storing incoming unprocessed raw digital signals transmitted from the A/D converters 138. Storing such signals enables multiple evaluations to be performed using a single set of incoming data, e.g., for purposes of improving quality of subsequently processed digital signals.

The image reconstruction and evaluation section 143 serves several functions. One function is to translate raw analog data signals transmitted from ultrasonic transducer array 102 and preliminarily processed by analog processing section 107 into a series of A-ScanSums. The A-ScanSums serve as a basis for ultrasonic test evaluation, performed in the secondary digital processing section 142, specifically in evaluation units 1-L, whose results may be used to interact with automation systems or image maps like B-Scans or C-Scans known to those skilled in the art. Collectively, the series of A-ScanSums form a raw virtual image of the physical item 101. The image reconstruction and evaluation section 143 processes the raw virtual image to remove noise by optimizing echoes created by features within the physical item 101 that might serve as reflectors of the ultrasonic waves being emitted into the physical item 101. Such reflectors can represent flaws within the physical item 101. The functions ascribed to the secondary digital processing section 142 may be performed by any suitable processor devices configured to enable the secondary digital processing section 142 to function as described herein.

As in the analog processing section 107 and the primary digital processing section 140, the secondary digital processing section 142 includes functions related to the creation of the waveforms that the ultrasonic transducer array 102 transmits into the physical item 101, as well as functions related to processing of waveforms reflected from the physical item 101 and received by the ultrasonic transducer array 102. A cycle control unit 164 is coupled to the transmitter settings unit 156 via a connection 166, and is coupled to the summation unit 158 via a plurality of connections 168. The evaluation units 170 are coupled via connections 172 to the summation unit 158 and to the cycle control unit 164 via a connection 174.

The cycle control unit 164 is coupled to a higher level processing unit 176, located in the upper level control section 144, via a connection 178. The evaluation units 170 are coupled to the higher level processing unit 176 via connection(s) 180.

The cycle control unit 164 is configured to regulate operations of the system 100. Specifically, the system 100 functions in a series of cycles. Each cycle includes a set of specifically configured ultrasonic pulses (or "tone bursts") emitted from each of the ultrasonic transceiver elements 110, followed by a pause, followed by the receipt of a series of reflected sound waves by each of the ultrasonic transceiver elements 110, which are, in turn, converted by the analog processing section 107 into a series of digital signals to be processed by the digital processing section 106. Data corresponding to each set of ultrasonic pulses is stored in the cycle control unit 164 in the form of a table (a "cycle table") that defines various characteristics of each series of pulses, such as the number of "shots" to be taken, the directions in which each shot is taken, the number of positions around the physical item 101 that shots are to be taken, etc.

The evaluation units 170 perform ultrasonic test evaluations on raw virtual images created and stored in the summation unit 158, or results deduced therefrom, according to techniques known to those skilled in the art. Each raw virtual image represents a plurality of ultrasonic reflections of ultrasonic "shots" taken at a predefined series of time intervals and a plurality of positions about the physical item 101 to generate a three-dimensional ultrasonic "field."

An additional function of the evaluation units 170 is correlation of data acquired during testing with positions on the physical item 101. Specifically, position encoders (not shown) are coupled to the ultrasonic transducer array 102 and to the digital processing section 106, to report and record positions of the ultrasonic transducer array 102 relative to the physical item 101. Analysis of the ultrasonic field includes, for example, selection of a segment or "slice" in time (also referred to as a "gate"). The gate is analyzed to determine the largest sound wave amplitude within the gate, and a measured time of flight associated with that amplitude.

As used herein, "time of flight" of an echo refers to the amount of time required for a sound wave to travel through the physical item 101 and back from an echo generating feature of the physical item. The selected amplitude is compared to a predefined reference amplitude, and the measured time of flight is compared to a predefined reference time of flight. If the selected amplitude exceeds the value of the reference amplitude, then a defect is deemed to be present at a physical location within the physical item 101 that is associated with the selected gate. Likewise, defects can be detected by evaluating the time of flight. For example, a measured time of flight associated with a selected gate that registers below the predefined reference time of flight may be indicative that the strength of the material in the physical item 101 at the associated location is too low (e.g., due to internal corrosion at that location). Alternatively, for situations in which corrosion is present on an external surface of the physical item 101, the measured time of flight may be greater than the predefined reference time of flight.

The higher level processing unit 176 includes PCs, desktop systems, stand-alone CPUs, and/or other systems that use the evaluations generated by the evaluation units 170 to perform various tasks such as recording data regarding the physical item 101, stimulating a process control, and/or generating a visualization for a user. In addition, the higher level processing unit functions as a command center for the system 100, wherein a user inputs instructions and data, such as data regarding the physical item 101, and parameters for causing the waveform shaping section 141 to create signals that will induce, in the physical item 101, the desired acoustic image tailored to cause potential reflectors in the material to optimally reflect acoustic waves for reception by the system 100 and subsequent processing of those acoustic waves. In some embodiments, specific types of acoustic waves, such as Rayleigh Waves or Lamb Waves, are excited within the physical item 101.

The higher level processing unit 176 also includes display devices 182 (e.g., two- and three-dimensional visual displays), user input devices 184 (e.g., keyboards, touchscreens, etc.), communications interfaces 186, and other equipment associated with ultrasonic materials analysis as known to those skilled in the art. A user provides input to the cycle control unit 164 via the input devices 184. The functions of the upper level control section 144 are performed on a computer, which may be of any suitable configuration sufficient to enable the system 100 to function as described herein. The higher level processing unit 176 receives processed digital data from the secondary digital processing section 142, and translates the data into visual displays that may be configured by a user through a suitable user interface programmed into the higher level processing unit 176, including functions such as providing correct "false color" for two-dimensional displays, three-dimensional displays, and creation of charts, etc. In addition, the higher level processing unit 176 performs additional evaluation functions that are enabled after a complete testing of the physical item 101 has been performed, such as the creation of analytical reports, and so forth.

The various modules, units, components, etc. of the system 100 can be implemented in hardware, software, firmware, and any combination thereof. For example, portions of the system can be implemented using a processor. As used herein, the term "processor" can include a microcontroller, a microcomputer, a programmable logic controller (PLC), a field-programmable gate array (FPGA), an application specific integrated circuit (ASIC), integrated circuits generally referred to in the art as a computer, and other programmable circuits, and these terms are used interchangeably herein. The processor can be coupled to a memory, which can include a random access memory (RAM), a read-only memory (ROM), a flash memory, a compact disc-read only memory (CD-ROM), a magneto-optical disk (MOD), a digital versatile disc (DVD), a non-transitory computer readable storage medium, and so forth.

The memory can store instructions for execution by the processor to implement the systems disclosed herein or to execute the methods disclosed herein.

As noted above, signals generated by the processing system 104 cause the ultrasonic transducer array 102 to emit ultrasonic tone bursts that are non-homogeneous across a width and breadth of ultrasonic transducer array 102.

Figure 4:
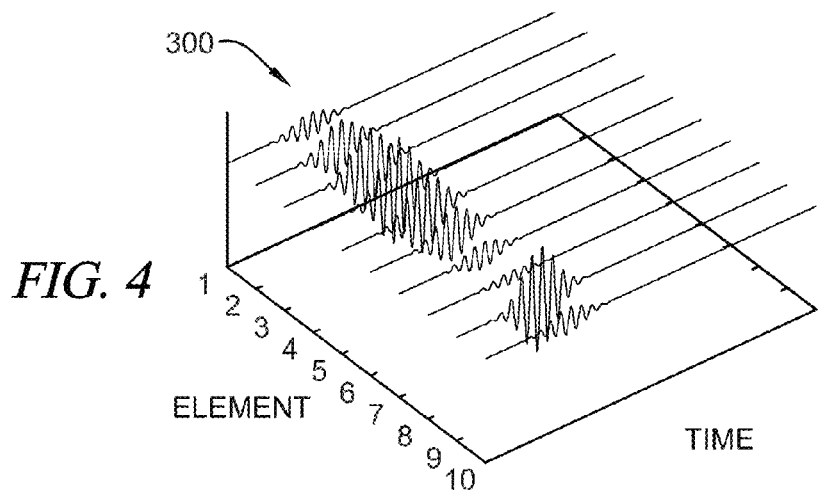
FIG. 4 is a perspective graphic representation of an exemplary series of waveforms used in an exemplary ultrasonic holography imaging system.
Figure 5:
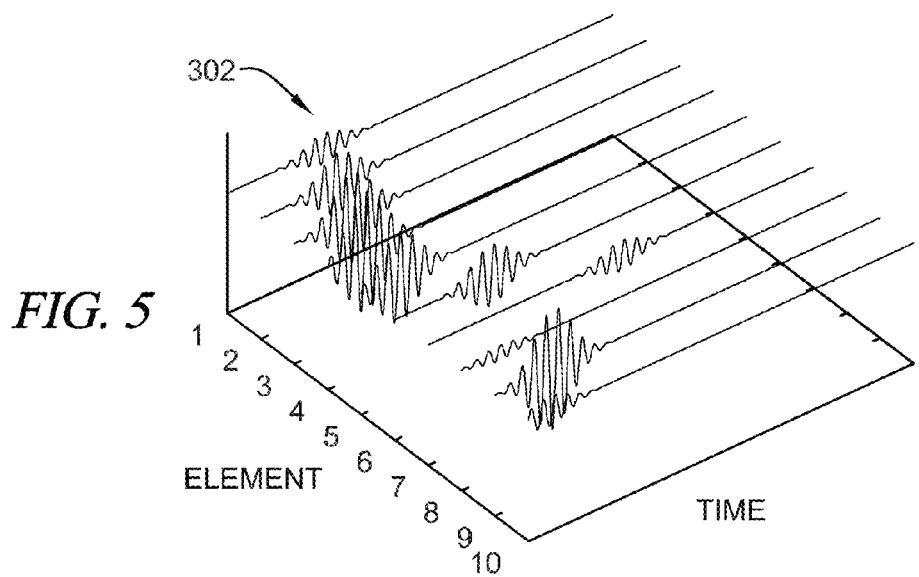
FIG. 5 is a perspective graphic representation of another exemplary series of waveforms used in an exemplary ultrasonic holography imaging system.
Figure 6:
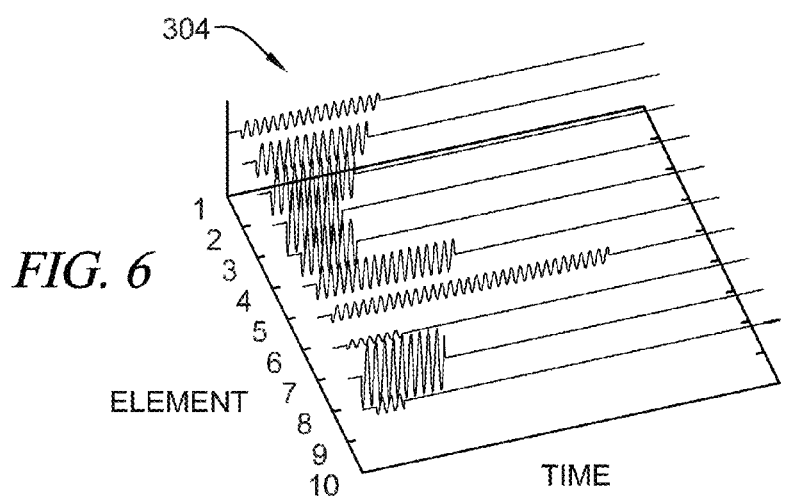
FIG. 6 is a perspective graphic representation of yet another exemplary series of waveforms used in an exemplary ultrasonic holography imaging system.

FIGS. 4-6 illustrate different configurations of waveforms, and wave fronts, that are provided by the system 100. FIG. 4 is a perspective graphic view of a series of waveforms 300 illustrating a first mode of variation of tone bursts. For simplicity of illustration, tone bursts from a single row of the ultrasonic transceiver elements 110 are illustrated. Specifically, the waveforms 300 represent tone bursts that vary in amplitude, but are constant in duration and time of emission. FIG. 5 illustrates a second mode of variation of tone bursts in which a plurality of waveforms 302 represent tone bursts that vary in amplitude, and in time of emission ("time shift"), but are constant in duration. FIG. 6 illustrates a series of waveforms 304 that represent a series of tone bursts that are time shifted, and variable in amplitude and duration.

Figure 7:
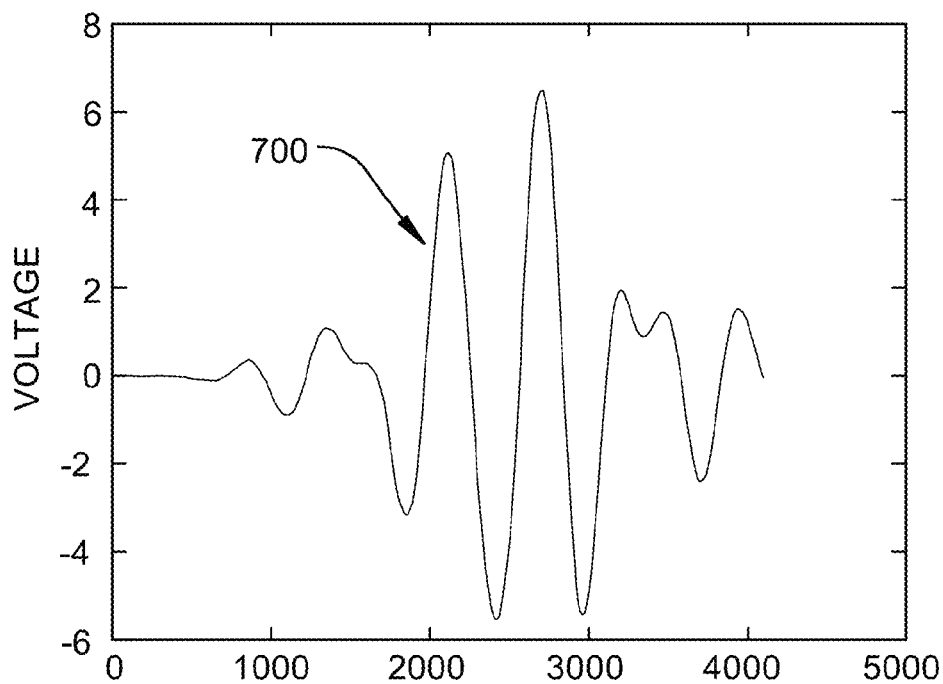
FIG. 7 is a plot of voltage as a function of time for an exemplary fully-analog excitation pulse used in an exemplary ultrasonic holography imaging system.

In order to produce the tone bursts shown in FIGS. 4-6, excitation signals are applied to the ultrasonic transceiver elements 110. FIG. 7 illustrates an exemplary excitation signal in the form of an arbitrary fully-analog excitation pulse 700. It will be appreciated that, in practice, the circuitry and components required to accurately and consistently produce the excitation pulse shown in FIG. 7 involves a significant degree of complexity, production cost, power consumption, and so forth. In addition, modules for generating such pulses are not readily amenable to implementation using ASICs and are limited in terms of voltage and speed.

Accordingly, the system 100 can be configured, in some embodiments or in some modes of operation, to supply multi-level square wave excitation pulses to the ultrasonic transceiver elements 110, instead of fully-analog excitation pulses of the type shown in FIG. 7.

Figure 8:
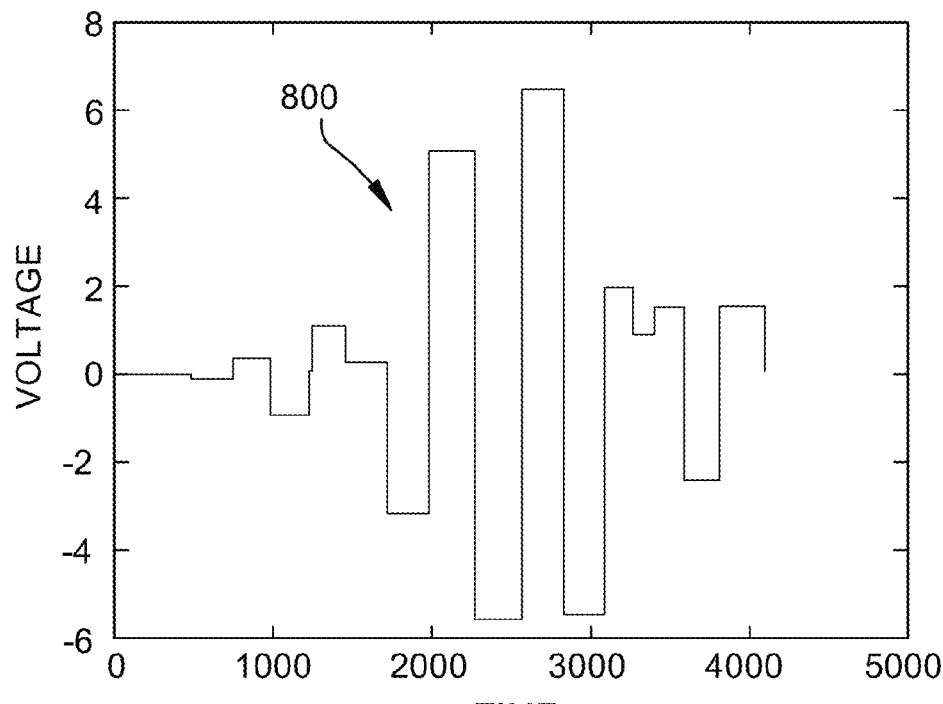
FIG. 8 is a plot of voltage as a function of time for an exemplary multi-level square wave excitation pulse used in an exemplary ultrasonic holography imaging system.

FIG. 8 illustrates an exemplary multi-level square wave excitation pulse 800. The illustrated pulse includes a plurality of square or rectangular pulses or steps at discrete positive and negative amplitude levels. In some embodiments, the multi-level square wave excitation pulse has a plurality of positive rectangular steps and a plurality of negative rectangular steps.

Figure 9:
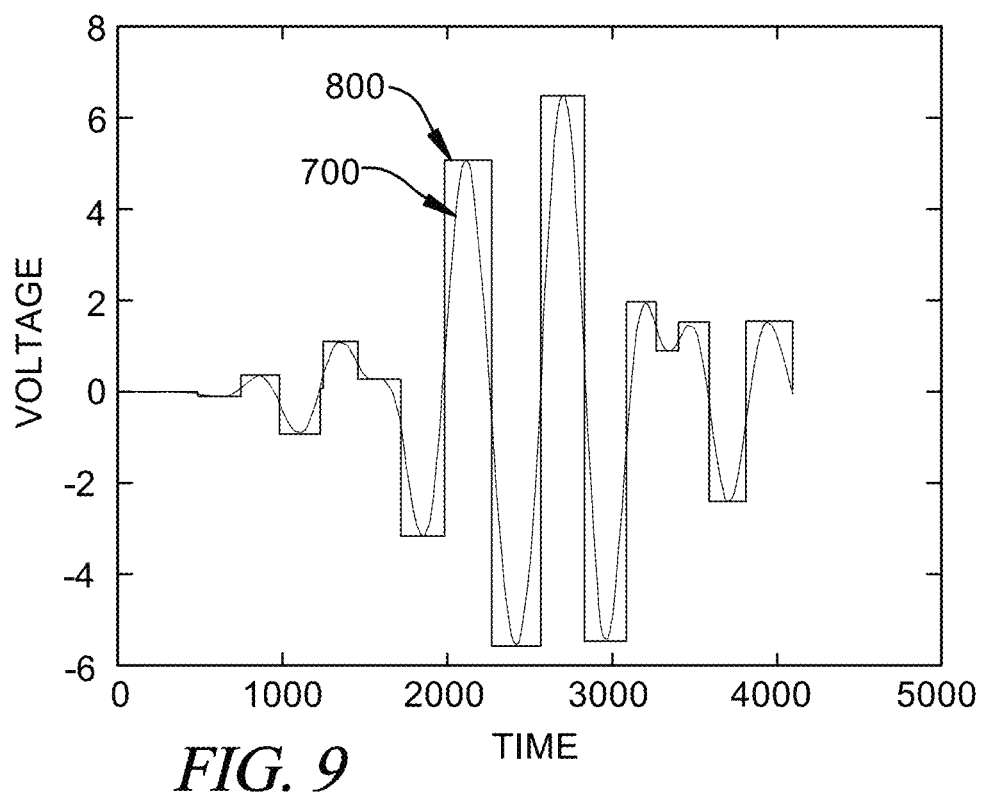
FIG. 9 is a plot of voltage as a function of time for the excitation pulse of FIG. 7 and the excitation pulse of FIG. 8.

The excitation pulses of FIGS. 7 and 8 are shown in FIG. 9 overlain on one another. As shown, the positive and negative square peaks or steps of the multi-level square wave excitation pulse 800 correspond in amplitude to the positive and negative peaks of the analog excitation pulse 700. In addition, the width of the positive and negative square peaks or steps of the multi-level square wave excitation pulse 800 correspond to the width between inflection points of the analog excitation pulse 700. Further, the pulses 700, 800 are phase aligned such that the transitions from one step to the next in the multi-level square wave excitation pulse 800 are aligned in time with the inflection points of the analog excitation pulse 700. It will thus be appreciated that the configuration of the multi-level square wave excitation pulse 800 can be selected by rectangular step sampling a corresponding fully-analog waveform 700.

The response of the ultrasonic transceiver elements to an excitation signal is inherently analog and cannot respond instantaneously to the step changes in voltage of the multi-level square wave excitation pulse 800. In other words, even though a multi-level square wave is used as the excitation pulse, the transceivers will not emit the same multi-level square wave. Rather, the actual ultrasonic waveform emitted will be the convolution of the multi-level square wave excitation pulse and the delta-response function of the transducer. Assuming the transducer response is a Gaussian function, the ultrasonic waveform emitted will closely resemble the desired ultrasonic waveform, even though a multi-level square wave excitation pulse is used in place of a fully-analog waveform.

Accordingly, the output of an ultrasonic transceiver element to which the multi-level square wave excitation pulse 800 is applied can be identical or substantially identical to what the output would have been had the counterpart fully-analog pulse been applied. In addition, the multi-level square wave excitation pulses can be selected by performing de-convolution processing based on the desired ultrasonic waveform and the delta-response function of the transducer.

The system 100 is thus configured to provide a comparable transceiver output using multi-level square wave excitation pulses, while at the same time reducing power consumption, system complexity, and/or cost as compared with systems that use fully-analog excitation pulses.

Figure 10:
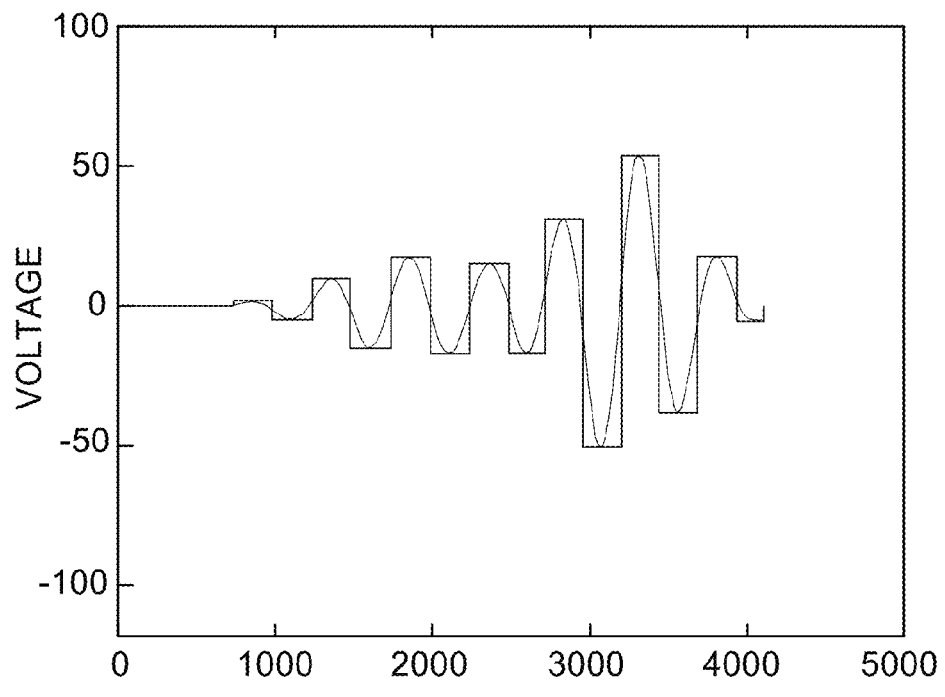
FIG. 10 is a plot of voltage as a function of time for an exemplary multi-level square wave excitation pulse and a counterpart fully-analog excitation pulse used in an exemplary ultrasonic holography imaging system.
Figure 11:
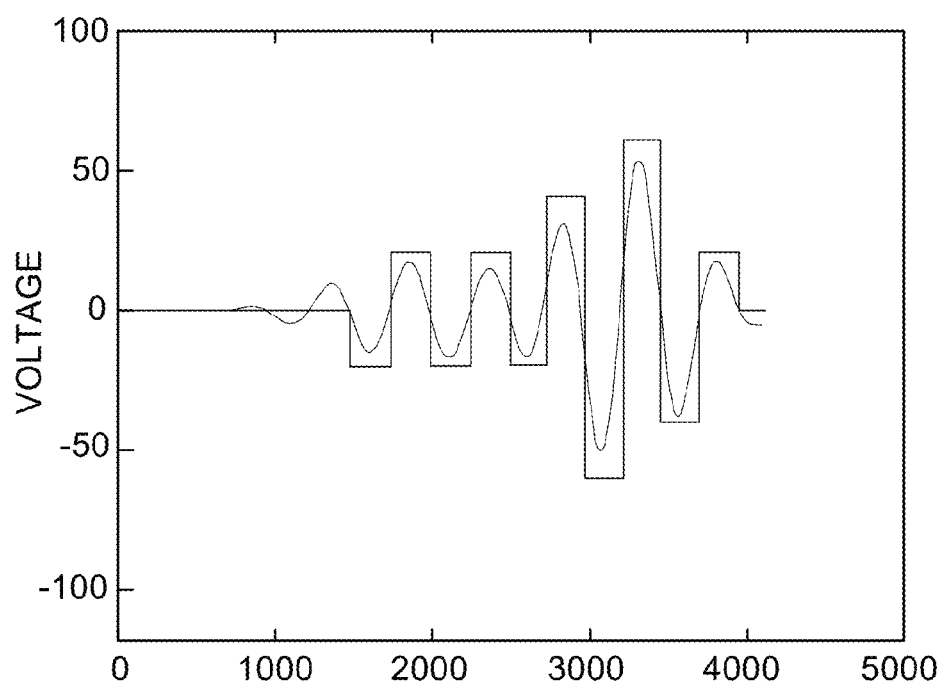
FIG. 11 is a plot of voltage as a function of time for an exemplary multi-level square wave excitation pulse and a counterpart fully-analog excitation pulse used in another exemplary ultrasonic holography imaging system.

The degree to which the multi-level square wave excitation pulse corresponds to a counterpart fully-analog excitation pulse is limited by the number of possible voltage levels or steps that can be included in the multi-level square wave excitation pulse. As shown in FIG. 10, when the number of possible voltage levels is high, the amplitude of the steps in the multi-level square wave excitation pulse corresponds exactly or almost exactly to the amplitude of the peaks in the counterpart analog excitation pulse. On the other hand, when the number of possible voltage levels is reduced (e.g., as shown in FIG. 11), the peaks in the analog excitation pulse are mapped to the closest voltage level and the respective amplitudes may or may not correspond exactly. Generally speaking, the greater the number of possible voltage levels available to construct the multi-level square wave excitation pulse, the greater the degree to which the transceiver output triggered by said pulse will correspond to the output had a counterpart fully-analog excitation pulse been used. In some embodiments, the system 100 is configured to produce multi-level square wave excitation pulses with up to five discrete positive voltage levels, up to five discrete negative voltage levels, and up to one zero voltage level for a total of up to eleven steps (e.g., −100V, −80V, −60V, −40V, −20V, 0V, 20V, 40V, 60V, 80V, 100V). In other embodiments, the system can be configured to produce multi-level square wave excitation pulses with more or less than eleven steps, with only positive steps, with only negative steps, with an unequal number of positive and negative steps, and/or with or without a zero level step.

Figures 12, 13:
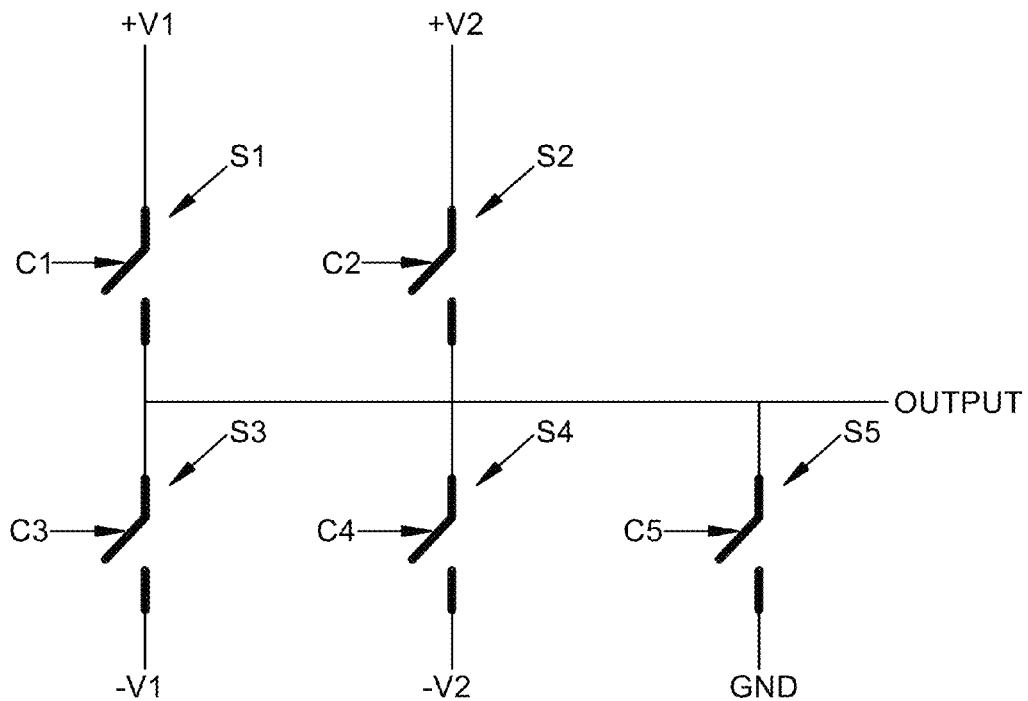
FIG. 12 is a circuit diagram illustrating a pulse generator portion of an exemplary ultrasonic holography system.
FIG. 13 is a partial truth table for the circuit of FIG. 12.

FIG. 12 is a schematic diagram of an exemplary circuit for generating multi-level square wave excitation pulses of the type described herein. The illustrated circuit is included in each of the pulse generators 146 (shown in FIG. 3) or each of the pulse train generators 146 (shown in FIG. 18). The circuit includes a plurality of switches (e.g., transistors such as MOSFETs) S1-S5 coupled between an output node and a plurality of voltage rails −V1, −V2, GND, +V1, +V2. A plurality of control lines C1-C5 control operation of respective ones of the switches S1-S5 to selectively place the output node in electrical communication with respective ones of the voltage rails. The control lines C1-C5 are controlled by digital logic circuitry (e.g., the transmitter controller 152) to change the voltage at the output node according to the partial truth table shown in FIG. 13. The circuit of FIG. 12 can thus produce a multi-level square wave excitation pulse with at least five discrete voltage levels or steps (i.e., −V1, −V2, GND, +V1, +V2). It is understood that the illustrated circuit can be readily modified to provide additional or fewer voltage steps.

Figure 14:
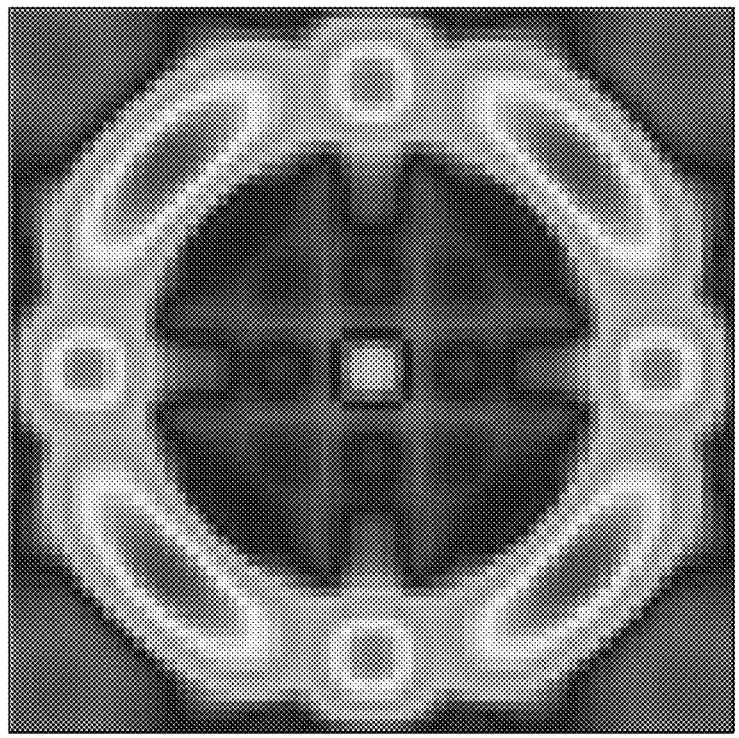
FIG. 14 is a simulated mapping of the output of an exemplary transducer array when fully-analog excitation signals are used to drive the transducer array to create an arbitrary sound field.
Figure 15:
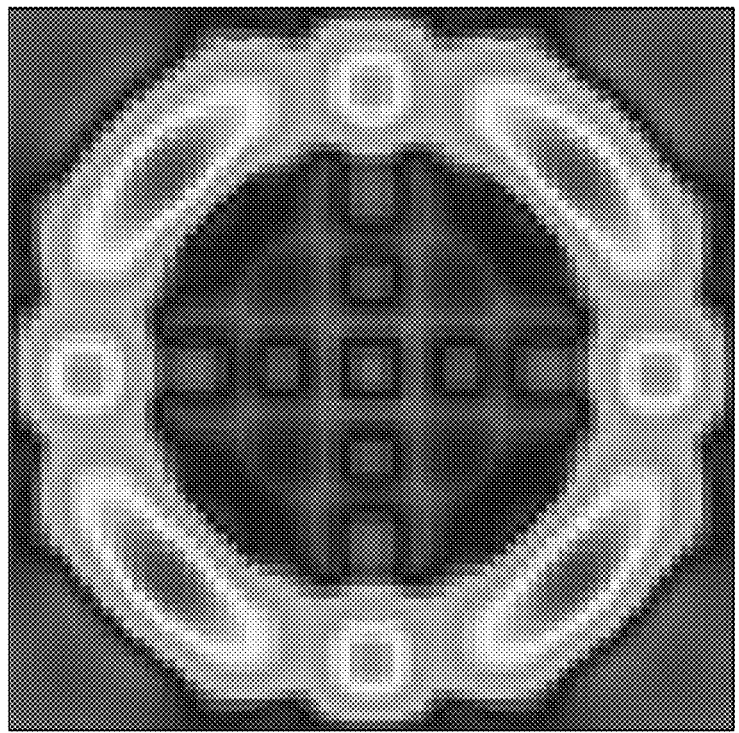
FIG. 15 is a simulated mapping of the output of an exemplary transducer array when multi-level square wave excitation signals are used to drive the transducer array to create an arbitrary sound field.

A simulated exemplary acoustic holography output generated by the system 100 when fully-analog excitation pulses are used is shown in FIG. 14. As shown in FIG. 15, there is a high degree of similarity in the output of the system 100 when multi-level square wave excitation pulses with up to eleven steps are used instead. Of course, the degree of similarity can be optimized by using additional or fewer steps as described above.

Figure 16:
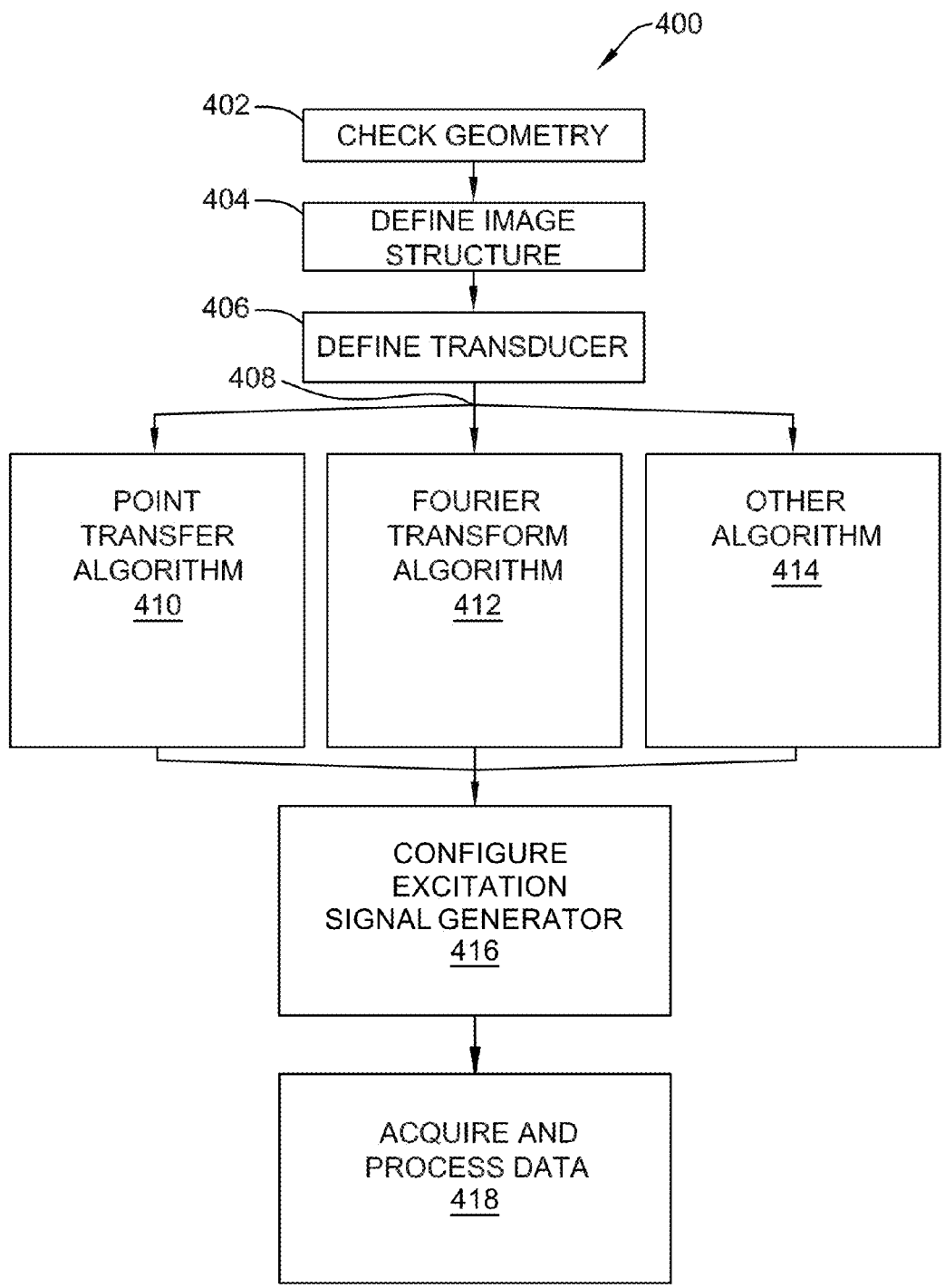
FIG. 16 is a flowchart illustrating an exemplary method for imaging a physical item using ultrasonic holography.

FIG. 16 illustrates an exemplary method 400 for performing imaging through ultrasonic holography. First, the geometry of the physical item 101 that is to be inspected is measured and the corresponding data is stored in the system 100 at step 402. Accordingly, areas of the physical item 101 that are known to be historically susceptible to defects in similar physical items are identified, enabling a desired image physical item to be defined in step 404. Once the geometry of the physical item 101 to be inspected and the desired image structure are known, a configuration of a transducer to obtain the desired acoustic image is defined in step 406. For example, a size of an array of piezoelectric elements is selected, an appropriate tone burst pulse frequency is selected, and individual piezoelectric element size and geometry is selected.

An appropriate data processing algorithm is selected in step 408 for use in converting the image structure defined at step 404 into a series of tone bursts having predefined individual configurations, with respect to each ultrasonic transceiver element 110. Several available data processing algorithms, adapted from optical imaging systems known to those skilled in the art, may be used, including a point transfer algorithm 410, a Fourier Transform algorithm 412, or other existing algorithms 414 for performing digital holography.

The selected data processing algorithm is used to transform the defined image structure into instructions to be transmitted to the waveform shaping section 141. For example, use of a point transfer algorithm 410 involves transforming a defined 404 image structure into an array of points in space, defining grayscale values for each point in the array, calculating a desired amplitude and phase for waveforms to be emitted that will impinge upon each point in the array, and providing coherent addition of contributions from each image point to determine the amplitude and phase of each tone burst from each element. The result of use of the point transfer algorithm 410 results in the definition of an interference pattern that the ultrasonic transducer array 102 will create upon emission of the defined series of tone bursts. Use of a Fourier Transform algorithm 412 can include transforming a defined image structure into an array of points in space, and calculating a Fourier transform of the defined image, using optical Fourier propagation to transfer the Fourier transform of the defined image to the ultrasonic transducer array 102. The result of use of the point transfer algorithm 410 or the Fourier Transform algorithm 412 results in the definition of an interference pattern that the ultrasonic transducer array 102 will create upon emission of the defined series of tone bursts, which then interferes to the real acoustic image.

Once the series of ideal tone bursts is defined, multi-level square wave excitation pulses which will cause the transducer array 102 to produce the ideal tone bursts or to produce tone bursts which are very similar to the ideal tone bursts are calculated in step 416. In particular, when the system is operating in the first mode of operation, the pulse generators 146 of the waveform shaping section 141 are configured or programmed to produce multi-level square wave excitation pulses which are rectangular-sampled approximations of a counterpart fully-analog excitation pulse. When the system is operating in the second mode of operation, the pulse generators 146 are configured or programmed to produce fully-analog excitation pulses. The mode of operation is user selectable or can be selected automatically by the system 100.

After a desired algorithm for processing data to be acquired is selected in step 408, and after the waveform shaping section 141 is configured in step 416 to produce the desired excitation signals, actual data acquisition occurs in step 418. During data acquisition in step 418, one or more ultrasonic pulses are emitted by the ultrasonic transducer array 102, with tone bursts emitted from different ones of the ultrasonic transceiver elements 110 varying in amplitude, duration, and/or time shift, as appropriate for the geometry of the physical item 101 being imaged and the predefined desired image structure. Reflected ultrasonic waves are received by the ultrasonic transceiver elements 110, and raw waveform signals are stored in the storage elements 161. The raw signals are amplified and pre-processed in the analog processing section 107 of the system 100 to produce A-scans, as described. Once generated, A-scans may be evaluated using known ultrasonic imaging techniques, for example to develop higher level visualizations, such as B-scans. As used herein, "B-scans" refers to a fully-developed, color scale three-dimensional image of an object. Data contained in A-scans may also be used in alarm systems through comparison with predefined threshold data. Finally, raw signals and processed signals obtained during an imaging session may be exported from the system 100 for data storage or additional evaluation.

While various methods disclosed herein may be shown in relation to flowcharts or sequence diagrams, it should be noted that any ordering of method steps implied by such flowcharts, sequence diagrams, or the description thereof is not to be construed as limiting the method to performing the steps in that order. Rather, the various steps of each of the methods disclosed herein can be performed in any of a variety of sequences. In addition, as the illustrated flowcharts and sequence diagrams are merely exemplary embodiments, various other methods that include additional steps or include fewer steps than illustrated are also within the scope of the present disclosure.

The systems and methods disclosed herein produce a number of advantages and/or technical effects. For example, in contrast to known ultrasonic holography systems, the ultrasonic holography imaging systems described herein are configured, in some embodiments, to generate and transmit non-homogeneous sound fields independent of transducer configuration. The ultrasonic holography imaging systems described herein enable, in some embodiments, the creation of real acoustic three dimensional images allowing the generation of a virtual image with improved definition and differentiation features, in comparison to known ultrasonic holography systems that work without the generation of a real acoustic image. In addition, the ultrasonic holography imaging systems described herein provide, in some embodiments, enhanced imaging that is capable of addressing the shape and configuration of the physical item being imaged. Furthermore, in contrast to known ultrasonic holography imaging systems, the systems and methods described herein provide, in some embodiments, for the creation of ultrasonic waveforms emitted from separate ultrasonic transceivers in an ultrasonic transducer array, such that at least two of the plurality of ultrasonic waveforms are differentiated from each other through variation of at least one of amplitude, frequency, time shift, and phase or modulations thereof. Further, the systems and methods described herein provide, in some embodiments, excitation of a transducer array using multi-level square wave excitation pulses which can be produced with reduced complexity, cost, and/or power consumption as compared with fully-analog excitation pulses, and which are less limited in terms of voltage, speed, and ASIC implementation flexibility.

Although the systems and methods disclosed herein are generally described in the context of ultrasonic holography for non-destructive testing, it will be appreciated that they have application in various other contexts. For example, the systems and methods disclosed herein can be used for ultrasonic holography in fields outside of non-destructive testing, as well as in various other measurement, monitoring, and control systems.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An ultrasonic holography system comprising:
    an ultrasonic transducer array including:
        a plurality of transmitter elements configured to emit a plurality of ultrasonic waveforms toward a physical item;
        a plurality of receiver elements configured to receive a plurality of return ultrasonic waveforms reflected from the physical item; and
        a processor system coupled to said ultrasonic transducer array, said processor system configured to:
            determine an analog ultrasonic holography tone burst signal;
            rectangular-step sample the analog ultrasonic holography tone burst signal to select a multi-level square wave tone burst signal;
            generate a plurality of outgoing multi-level square wave transmitter driving signals configured to cause said ultrasonic transducer array to emit said plurality of ultrasonic waveforms, wherein each of said plurality of ultrasonic waveforms are differentiated from the multi-level square wave tone burst signal through variation of at least one of amplitude, frequency, phase, time shift, and a modulation of any one thereof;
            receive a plurality of incoming analog waveform signals, generated by said ultrasonic transducer array, said incoming analog waveform signals representative of at least a portion of said plurality of return ultrasonic waveforms; and
            process the plurality of incoming analog waveform signals to evaluate the internal structure of the physical item.

2. The system of claim 1, wherein the plurality of transmitter elements and the plurality of receiver elements are formed as a plurality of common transceiver elements.

3. The system of claim 1, wherein the processor system is configured to process the plurality of incoming analog waveform signals by constructing a virtual image using the plurality of incoming analog waveform signals, the virtual image corresponding to at least a portion of an internal region of the physical item.

4. The system of claim 1, wherein at least two of said plurality of ultrasonic waveforms are differentiated from each other through variation of at least two of amplitude, frequency, phase, time shift, and a modulation of any one thereof.

5. The system of claim 1, wherein the processor system includes a pulse generator circuit configured to produce said multi-level square wave transmitter driving signals.

6. The system of claim 1, wherein the processor system is configured to generate multi-level square wave transmitter driving signals having a plurality of positive rectangular steps and a plurality of negative rectangular steps.

7. The system of claim 1, wherein the processor system is configured to generate multi-level square wave transmitter driving signals with up to five discrete positive voltage levels, up to five discrete negative voltage levels, and up to one zero voltage level.

8. The system of claim 1, wherein the processor system is configured to generate the plurality of multi-level square wave transmitter driving signals such that at least one of said signals is a rectangular-sampled approximation of a corresponding fully-analog driving signal.

9. The system of claim 8, wherein the at least one signal includes a plurality of steps having amplitudes that correspond to amplitudes of counterpart peaks in the corresponding fully-analog driving signal.

10. The system of claim 9, wherein the plurality of steps are selected from a finite set of discrete voltage levels.

11. The system of claim 10, wherein, for each peak in the corresponding fully-analog driving signal, a step selected from the finite set that is closest in voltage to the peak is included in the at least one signal.

12. The system of claim 8, wherein the at least one signal includes a plurality of steps having widths that correspond to widths between counterpart inflection points in the corresponding fully-analog driving signal.

13. The system of claim 8, wherein transitions between steps in the at least one signal correspond in phase to counterpart inflection points in the corresponding fully-analog driving signal.

14. The system of claim 1, wherein the plurality of multi-level square wave transmitter driving signals are selected by performing de-convolution of the pulse response of the transducer array from a desired ultrasonic waveform.

15. The system of claim 1, wherein the processor system is configured to execute a holographic reconstruction algorithm using the plurality of incoming analog waveform signals.

16. A method for imaging a physical item using ultrasonic holographic imaging, comprising:
    using a processor system coupled to a memory device;
    defining an image structure using data stored in the memory device, the data representing a geometry of the physical item;
    determine an analog ultrasonic holography tone burst signal;
    rectangular-step sample the analog ultrasonic holography tone burst signal to select a multi-level square wave tone burst signal;
    driving a plurality of ultrasonic transmitter elements of a transducer array coupled to the processor system with a plurality of multi-level square wave transmitter driving signals to cause the ultrasonic transducer array to emit a plurality of ultrasonic waveforms, wherein each of the of ultrasonic waveforms are differentiated from the multi-level square wave tone burst signal through variation of at least one of amplitude, frequency, phase, time shift, and a modulation of any one thereof.

17. The method of claim 16, further comprising:
emitting into the physical item, with the ultrasonic transducer array, the plurality of ultrasonic waveforms;
receiving, with the ultrasonic transducer array, a plurality of ultrasonic waveforms reflected from the physical item; processing, with the processor system, the plurality of reflected ultrasonic waveforms to produce a plurality of digital A-Scans; and
evaluating, with the processor system, the plurality of digital A-scans.

18. The method of claim 16, wherein at least two of the ultrasonic waveforms are differentiated from each other through variation of at least two of amplitude, frequency, phase, time shift, and a modulation of any one thereof.

19. The method of claim 16, wherein the processor system includes a pulse generator circuit configured to produce said multi-level square wave transmitter driving signals.

20. The method of claim 16, wherein said driving comprises generating multi-level square wave transmitter driving signals having a plurality of positive rectangular steps and a plurality of negative rectangular steps.

21. The method of claim 16, wherein said driving comprises generating multi-level square wave transmitter driving signals with up to five discrete positive voltage levels, up to five discrete negative voltage levels, and up to one zero voltage level.

22. The method of claim 16, wherein said driving comprises generating at least one signal that is a rectangular-sampled approximation of a corresponding fully-analog driving signal.

23. A system, comprising:
an ultrasonic transducer array including a plurality of transmitter elements configured to emit a plurality of ultrasonic waveforms;
a processor system coupled to said ultrasonic transducer array, said processor system configured to:
determine an analog ultrasonic holography tone burst signal;
rectangular-step sample the analog ultrasonic holography tone burst signal to select a multi-level square wave tone burst signal;
a pulse generation circuit configured to generate a plurality of multi-level square wave transmitter driving signals configured to cause said ultrasonic transducer array to emit said plurality of ultrasonic waveforms, wherein each of said plurality of ultrasonic waveforms are differentiated from the multi-level square wave tone burst signal through variation of at least one of amplitude, frequency, phase, time shift, and a modulation of any one thereof.

* * * * *